(12) United States Patent
Vo-Dinh

(10) Patent No.: US 6,219,137 B1
(45) Date of Patent: *Apr. 17, 2001

(54) NANOPROBE FOR SURFACE-ENHANCED RAMAN SPECTROSCOPY IN MEDICAL DIAGNOSTIC AND DRUG SCREENING

(75) Inventor: Tuan Vo-Dinh, Knoxville, TN (US)

(73) Assignee: Lockheed Martin Energy Research Corporation, Oak Ridge, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/205,773

(22) Filed: Dec. 3, 1998

(51) Int. Cl.$^7$ .................................................. G01J 3/44
(52) U.S. Cl. ................ 356/301; 204/157.15; 356/300; 356/301; 501/54; 536/24.31; 128/719; 359/370; 364/559; 435/6; 435/183; 435/325; 435/29; 435/172; 435/287.2; 435/287.9; 435/288.7; 435/91.2; 436/172; 436/20; 436/525; 436/805; 436/801; 436/536; 436/518; 514/492; 514/188; 210/198.2; 600/310
(58) Field of Search ................ 435/6, 18.3, 172, 435/325, 29, 287.2, 287.9, 288.7, 91.2; 436/172, 20, 525, 805, 801, 536, 518; 514/492, 188; 210/198.2; 600/310; 204/157.15; 356/300, 301; 501/54; 536/24.31; 128/719; 359/370; 364/559; 606/17

(56) References Cited

U.S. PATENT DOCUMENTS

| | | | | |
|---|---|---|---|---|
| 5,567,628 | * | 10/1996 | Tarcha et al. | 436/525 |
| 5,817,462 | * | 10/1998 | Garini et al. | 435/6 |
| 5,864,397 | * | 1/1999 | Vo-Dinh | 356/301 |

OTHER PUBLICATIONS

Tuan Vo–Dinh, "Surface–enhanced Raman spectroscopy using metallic nanostructures", *Trends in Analytical Chemistry*, vol. 00, No. 0, pp. 1–26 (1998).

* cited by examiner

Primary Examiner—Christopher S. F. Low
Assistant Examiner—Hope A. Robinson
(74) Attorney, Agent, or Firm—Quarles & Brady LLP

(57) ABSTRACT

A probe for a surface-enhanced Raman scattering spectrometer is provided for injection into a cell in order to detect trace amounts of a compound within that cell. The probe has a spherical shape with a diameter less than one micrometer and preferably in the 10–500 nanometer range. The nanoprobes can have a receptor coating related to the specific compound to be detected by the probe. A process for producing, injecting and utilizing the nanoprobes are described.

29 Claims, 4 Drawing Sheets

NANOPROBE FOR SURFACE-ENHANCED RAMAN SPECTROSCOPY IN MEDICAL DIAGNOSTIC AND DRUG SCREENING

BACKGROUND OF THE INVENTION

The present invention relates to Raman spectroscopy and surface-enhanced Raman spectroscopy; and more particularly to surface-enhanced Raman medical (SERMED) diagnostic instruments and methods for non-invasive medical diagnosis and drug screening.

Normal Raman spectroscopy relates to the scattering of light by a gas, liquid or solid with a shift in frequency or wavelength from that of the usually monochromatic incident radiation. Upon irradiation of a molecule with light in biological applications, the incident radiation having a frequency $v$ should produce scattered radiation, the most intense part of which has unchanged frequency (Rayleigh scattering). In addition, if the polarization of a molecule changes as it rotates or vibrates, there are spectral lines of much lesser intensity at frequencies $v \pm v_k$, where $v_k$ is the molecular frequencies of rotation or vibration.

Fleischmann et al. first reported strongly enhanced Raman scattering from pyridine molecules adsorbed on silver electrode surfaces that had been roughened electrochemically by oxidation-reduction cycles (*Chem. Phys. Lett.* 26, 163, 1974). This increase in Raman signal, originally attributed to a high surface density produced by the roughening of the surface of electrodes, was later identified by Jeanmaire and Van Duyne (*J. Electroanal. Chem.* 84, 1, 1977) and independently by Albrecht and Creighton (*J. Am. Chem. Soc.* 99, 5215, 1977) as a direct result of a surface-enhancement process, hence the term surface-enhanced Raman scattering (SERS) effect.

There are at least two major types of mechanisms that contribute to the SERS effect: a) an electromagnetic effect associated with large local fields caused by electromagnetic resonances occurring near metal surface structures, and b) a chemical effect involving a scattering process associated with chemical interactions between the molecule and the metal surface. It has been shown that electromagnetic interactions between the molecule and the substrate provide one of the dominant enhancements in the SERS process. Such electromagnetic interactions are divided into two major classes; interactions that occur only in the presence of a radiation field, and interactions that occur even without a radiation field. The first class of interactions between the molecule and the substrate are believed to play a major role in the SERS process. A major contribution to electromagnetic enhancement is due to surface plasmons. Surface plasmons are associated with collective excitations of surface conduction electrons in metal particles. Raman enhancements result from excitation of these surface plasmons by the incident radiation. At the plasmon frequency, the metal becomes highly polarizable, resulting in large field-induced polarizations and thus large local fields on the surface. These local fields increase the Raman emission intensity, which is proportional to the square of the applied field at the molecule. Additional enhancement is due to excitation of surface plasmons by the Raman emission radiation of the molecule.

Surface plasmons are not the only sources of enhanced local electromagnetic fields. Other types of electromagnetic enhancement mechanisms are concentration of electromagnetic field lines near high-curvature points on the surface, i.e., the "lightning rod" effect, polarization of the surface by dipole-induced fields in absorbed molecules, i.e., the image effect, and Fresnel reflection effects.

The chemical effect is associated with the overlap of metal and adsorbate electronic wave functions, which leads to ground-state and light-induced charge-transfer processes. In the charge-transfer model, an electron of the metal, excited by the incident photon, tunnels into a charge-transfer excited state of the adsorbed molecule. The resulting negative ion (adsorbate molecule-electron) has a different equilibrium geometry than the original neutral adsorbate molecule. Therefore, the charge-transfer process induces a nuclear relaxation in the adsorbate molecule which, after the return of the electron to the metal, leads to a vibrationally excited neutral molecule and to emission of a Raman-shifted photon. The "adatom model" also suggests additional Ramon enhancement for adsorbates at special active sites of atomic-scale roughness, which may facilitate charge-transfer enhancement mechanisms.

SUMMARY OF THE INVENTION

A general object of the present invention is to provide a surface-enhanced Raman spectroscopic technique, that increases Raman emission due to the surface-enhanced Raman scattering effect and can be used inside microsize structures, such as cells.

Another object is to provide a probe for such a technique which can be delivered into a biological, chemical or physical structure to provide surface-enhanced Raman emission. The SERS effect and its applications have been reviewed by T. Vo Dinh, "*Surface-enhanced Raman spectroscopy using metallic nanostructures*", *Trends in Analytical Chemistry*, 1998.

A further object of the present invention is to provide such a probe which is less than one micrometer in size.

Yet another object is to provide methods for injecting the probe into such microscopic structures.

These and other objectives are satisfied by a probe for a surface-enhanced Raman scattering monitor or spectrometer which is suited to detect trace quantities of toxic chemicals and related biological indicators. The nanometer size of these probes allows them to be delivered inside organisms and even a single cell to serve as intracellular self-contained sensors, thereby extending the usefulness and application of the SERMED probes to the realm of intracellular medical diagnosis, as well as extra-cellular diagnosis.

The nanoprobe of the present invention comprises a metallic system which provides the SERS effect and a chemical/biological system which provides selective binding within the cell. The nanoprobe has a metallic core which optionally may be magnetic or electrically charged materials. For example the core may be solely metallic material or a non-metallic material with a metallic coating. Preferably the core has an external coating formed of a polymer, a biological material (such as an antibody, enzyme or DNA) or biometric material (e.g. PNA, cyclodextrins or molecular imprint). A nanoprobe can be constructed to sense a particular characteristic of the cell by having specific receptors that provide diagnostic information of different regions and species inside the cell. The receptors also can be selected to provide information regarding characteristics outside of the cells, on the outside surface of the cell, or inside the cells near the nucleus or other intracellular component.

Multiple nanoprobes can be used in high throughput screening for drug detection or medical diagnostics, whereby a large number of single cells can be analyzed simultaneously, each cell or group of cells can be analyzed simultaneously by one or more nanoprobes.

DETAILED DESCRIPTION OF THE INVENTION

The present surface-enhanced Raman medical (SERMED) diagnostic system utilizes extremely small probes to enhance Raman emission in order to detect trace material within a cell. Preferably the probes are spherically shaped, although other shapes may be employed. Because cell sizes range from one to ten micrometers, the present SERMED probes for intracellular use are 10 to 100 nanometers in diameter. For extra-cellular use, larger nanoprobes have typical diameters in the 30 to 500 nanometer range are used, but such probes can be up to substantially one micrometer in diameter. Because the probe typically is smaller than one micrometer (i.e. submicron), it is being referred to herein as a "nanoprobe".

With reference to FIGS. 1A–1G, the nanoprobe can have one of several embodiments depending upon the specific application for the probe. In the basic form shown in FIG. 1A, the nanoprobe comprises a spherical metal core 10 thus providing a probe with a metallic surface. As an alternative, this version of the nanoprobe can have a non-metallic core 12 with an outer metallic coating 14.

Figure 1A:
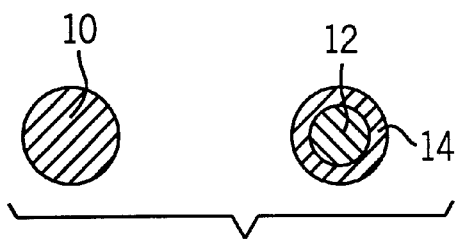
FIGS. 1A through 1G are cross sectional views of several embodiments of a surface-enhanced Raman scattering probe according to the present invention.
Figure 1B:
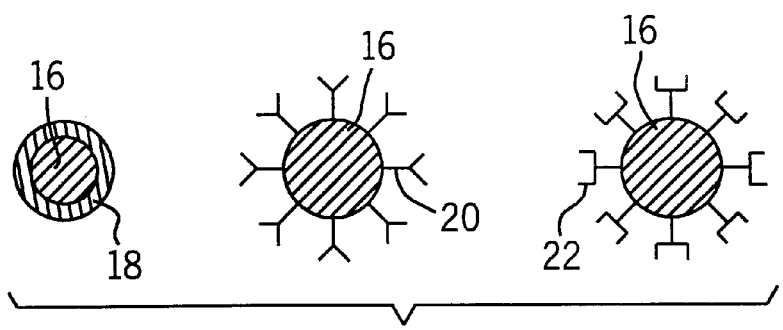

Another embodiment of the nanoprobe is illustrated in FIG. 1B and has a metallic core 16 covered with a coating 18, 20 or 22 which provides selective binding to the cell structure. The coating can comprise a polymer 18, or a bioreceptor 20, such as an antibody, a cell component, an enzyme or DNA. In addition, the external coating around the metal core 16 can comprise a biomimetic material 22.

Figure 1C:
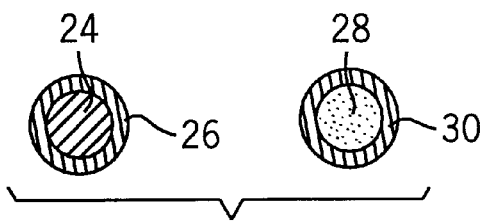

With reference to FIG. 1C, the nanoprobe may be formed by a magnetic core 24 with an outer coating of a metal 26 that induces the SERS effect. Another variation is the use of electrically charged material for the core 28 about which a similar metal coating 30 is applied. Magnetic or electrically charged cores allow remote manipulation of the nanoprobe using magnetic or electric fields to guide the nanoprobe inside the cells, and then to specific locations therein. Similarly the magnetic or electric field can be employed to remove a nanoprobe from the cell.

Figure 1D:
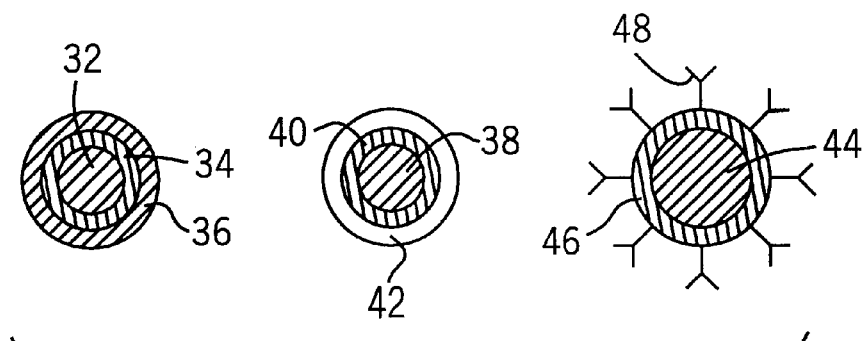

FIG. 1D illustrates the use of a magnetic core 32 having an external metal layer 34 about which an outer coating of a chemical or biological material 36 is applied. A variation of this structure utilizes a magnetic core 38 with a metal intermediate layer 40 over which a chemical coating 42 has been applied. Another variation of the basic structure of a magnetic core 44 and a metal coating 46 utilizes an exterior coating of a bioreceptor 48.

The chemical nanoprobe coatings include materials, such as polymers and chemical functional groups, that facilitate delivery and transport of the nanoprobes inside the media being investigated. A bioreceptor is employed to identify the target compound of the investigation via molecular recognition. The bioreceptors may be an enzyme, an antibody, a gene fragment, a chemoreceptor, a tissue, an organella, or a microorganism. The operation of the antibody probes is based on the antibody—antigen molecular recognition, and DNA probe operation is based on the hydridization process. Hydridization of nucleic acid probe to DNA biotargets (e.g., gene sequences, bacteria and viral DNA) offers a high degree of accuracy for identifying DNA sequences which are complimentary to that of the probe.

Figure 1E:
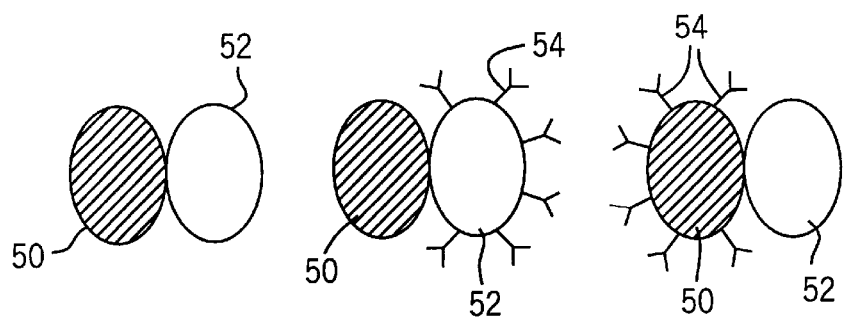

FIG. 1E depicts another nanoprobe configuration in which a metallic nano-particle 50 is adjacent to submicron non-metallic (receptor) material 52. For example the non-metallic material 52 may be a polymer, silica or titania. Variations of this configuration can coat either the metallic particle 50 or the non-metallic material 52 with a chemical or biological coating 54, previously described.

Figure 1F:
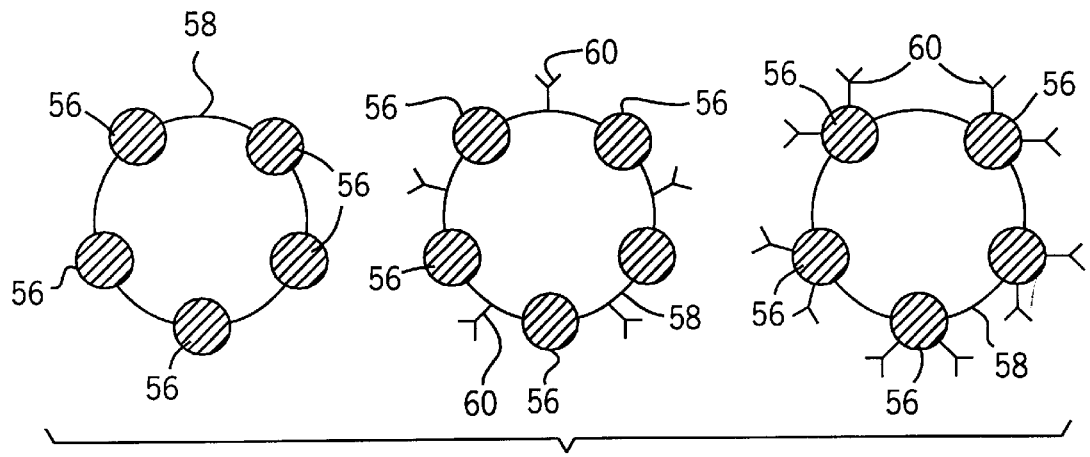

Referring to FIG. 1F, submicron metallic particles 56 also can be encrusted onto non-metallic material 58 to form the nanoprobe. Similarly a chemical or biological coating 60 of a bioreceptor or biomimetic material may be applied to the metallic particles 56 or the non-metallic material 58.

Figure 1G:
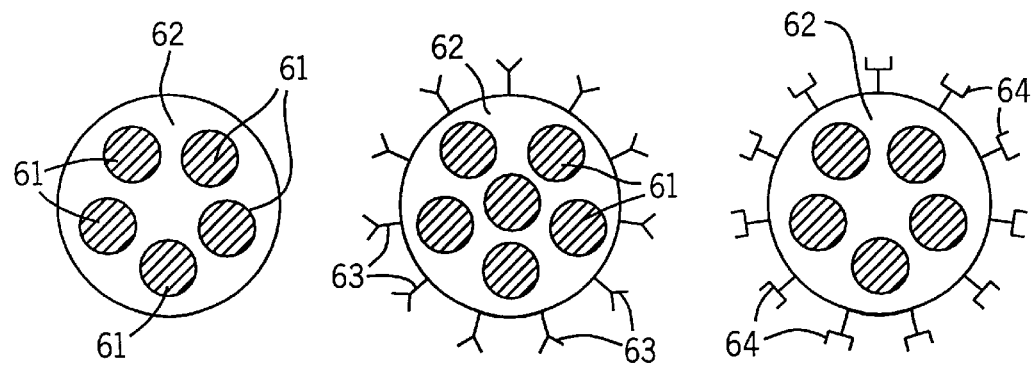

FIG. 1G depicts yet another embodiment of nanoprobes consisting of metallic nano-particles formed inside a non-metallic particle 62 with a chemical or biological coating 63. Alternatively a biometric material 64 may be applied.

The preparation of these nanoprobes involves depositing submicron (nano-sized) particles onto a substrate, such as a glass plate. The particles can comprise polystyrene latex spheres, fumed silica, titanium oxide or aluminum oxide particles. For example, this deposition is accomplished by placing a glass slide on spin coating device. A few drops of the submicron particles in a water solution is placed on the glass slide which is then immediately spun to distribute the material across the surface of the glass slide. The spinning precludes clumping of the particles on the glass surface and provides uniformly adhered coverage. The coverage of the particles can be controlled by varying the concentration of the nanoparticle solutions.

The second step in the process involves coating the particle-covered glass slide with silver. This is accomplished using a vacuum evaporator and in which the pressure in the evaporator during coating is less than $5 \times 10^{-6}$ torr. The rate of silver deposition is controlled between 1.5 and 2.0 nm/sec. The deposition rate and thickness of the silver can be measured with a Kronos model QM-311 quartz crystal thickness monitor. The nanospheres coated with silver are removed from the substrate and are ready for use as nanoprobes.

Among the techniques based on solid substrates, the methods using a simple submicron material, such as fumed silica, Teflon® or latex spheres, appear to be the simplest to prepare. Teflon® and latex spheres are commercially available in a wide variety of sizes. The shapes of these materials are very regular and their size can be selected for optimal enhancement of the SERS effect.

EXAMPLE 1

A 50 microliter volume of a suspension of latex or Teflon® submicron spheres was applied to the surface of a substrate. Various substrates were utilized, including filter paper, cellulosic membranes, glass plates and quartz materials. Next the substrate was placed on a high speed spinning device and spun at 800 to 2,000 RPM for 20 seconds. Silver then was deposited on the nanosphere coating in a vacuum evaporator at a deposition rate of 2 nm/second to form a silver layer having a thickness of 5 to 100 nm.

EXAMPLE 2

Titanium oxide was coated with silver as an alternative material for use with SERS. This technique was found to produce efficient Raman enhancement. Commercially available titanium oxide particles of the appropriate size were first deposited on glass and cellulose substrates in a water suspension of 10% concentration by weight. The titanium oxide particles then were coated with a 50 to 100 nm layer of silver by the previously described thermal evaporation process. The silver coated titanium oxide particles were removed from the substrate and found to be ready for SERS use.

EXAMPLE 3

Another type of nanoprobe material that is quite SERS active and easy to prepare is fumed silica based material. Fumed silica has been used as a thickening agent in various industrial processes and is commercially available. The fumed silica particles were suspended in a 10% water solution and coated onto a glass plate. The particles were coated with a 50 to 100 nm of silver by thermal expansion and then removed from the substrate. This technique also can be utilized to produce silver coated alumina nanoprobes.

EXAMPLE 4

Silver colloid hydrosol also produces an SERS active media in solution. Such colloid hydrosol has the advantage of ease of colloid formation and straight forward characterization of the colloid solutions by simple UV absorption. Silver colloids are generally prepared by rapid mixing a solution of $AgNO_3$ with ice-cold $NaBH_4$. Such colloid systems tend to coagulate which may adversely affect their use as nanoprobes. However, that coagulation problem can be minimized by stabilizers, such as poly(vinylalcohol), poly(vinylpyrrolidone) and sodium dodecyl sulfate. Nevertheless, use of such stabilizers can produce interferences and cannot be utilized inside cellular environments. A method that can minimize the coagulation problem involves coating the system with a monolayer of a chemical, such as a polymer, immediately after nanoparticles of silver sols are formed to stabilize their size and shape.

With respect to chemical and biological exterior coatings of the nanoprobes, DNA oligonucleotides can be attached readily since most of the SERS coatings are based on gold or silver. The binding of oligonucleotides to such metal surfaces can be based on thiol chemistry or other standard chemical binding methods. The thiols are known to strongly chemisorb to gold and silver surfaces to form monolayers that possess supramolecular properties. Peptide nucleic acid (PNA) can be used instead of DNA.

If the over coat of the nanoprobe is silica, the DNA probe is bound to the silica coating. The silica surface is derivatized with silan by incubation in a 2% 3-aminopropyl triethoxysilane (APTS) for 24 hours at room temperature, washed in acetone and dried in a vacuum. The silanyl groups are activated by incubation in 1% gutaraldehyde in water for one hour at room temperature. Excess gutaraldehyde is removed by washing in water and rinsing with phosphate buffered saline (PBS). The DNA probe molecules containing amino linkers are attached to the silica surface by incubating for 24 hours at 4° C. with a probe solution (e.g. concentration of 10 mg/mL). The unbound probe is washed away with PBS.

An alternative approach is to overcoat the SERMED nanoprobe surface with a thin layer of polymer. In this case, various bioreceptors can be bound to the polymer coating. Biomimetic material, such as cyclodextrins or molecular imprint, can be attached to such nanoprobes.

Figure 2A:
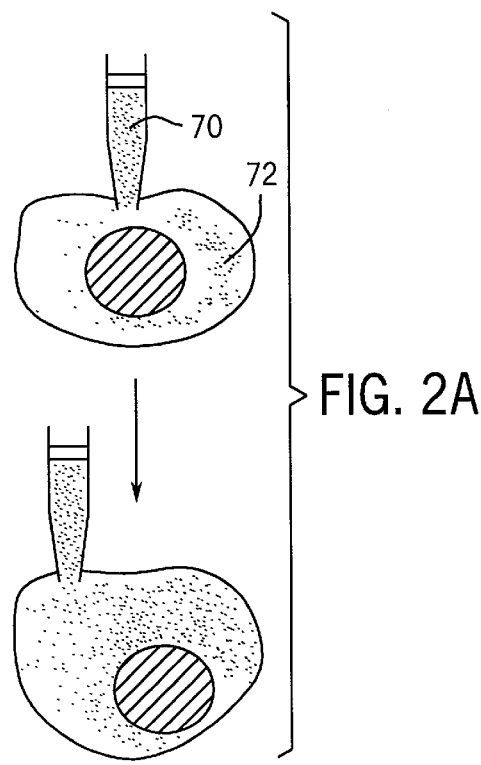
FIGS. 2A through 2D show alternative processes for introducing the probe into a biological cell.

Several methods can be employed to deliver the SERMED nanoprobes inside cells. With reference to FIG. 2A, SERMED nanoprobes in a solution can be injected through a micro injector 70 by applying appropriate pressure. Alternatively, if the nanoprobes are magnetic, such as those with magnetic cores, a magnetic field can be applied which drives the nanoprobes into the cell 72. If the nanoprobes are electrically charged, a voltage can be employed that propels the nanoprobes into the cells as an ionic current, a technique which is referred to as iontophoresis.

Figure 2B:
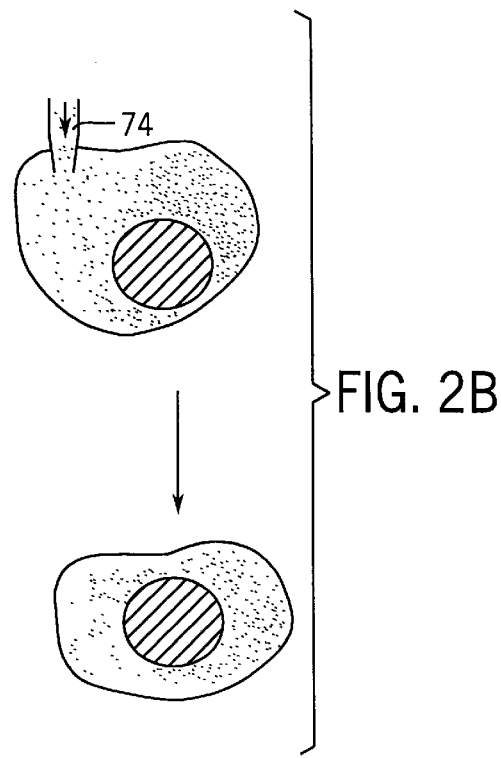

Another technique is illustrated in FIG. 2B in which a pressurized microjet 74 of an inert gas such as helium, containing an emulsion of nanoprobes, is used to inject the nanoprobes into the cell.

Figure 2C:
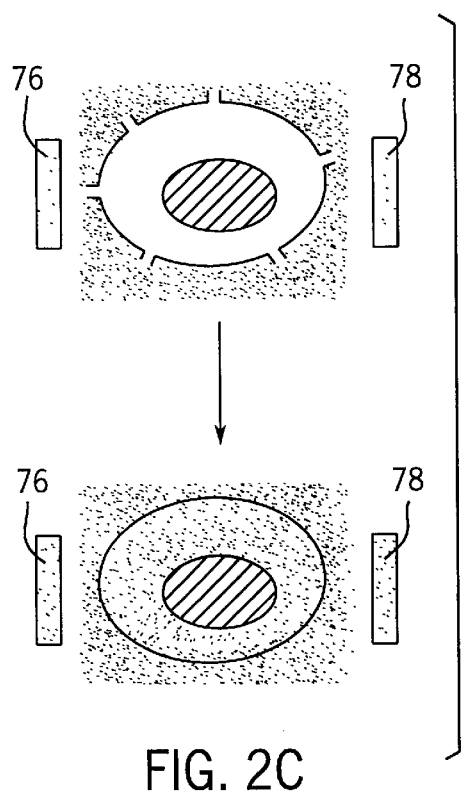

With reference to FIG. 2C another injection technique involves making the cell membrane transiently permeable to the outside solution containing the nanoprobes. This is accomplished by disrupting the membrane structure with a brief, but intense, electrical shock. For example, a pair of electrodes 76 and 78 are placed on opposite sides of the cell and 2,000 volts per centimeter is applied across the electrodes for 200 microseconds. This allows some of the nanoprobes to migrate into the cell and become retained there following the shock.

Figure 2D:
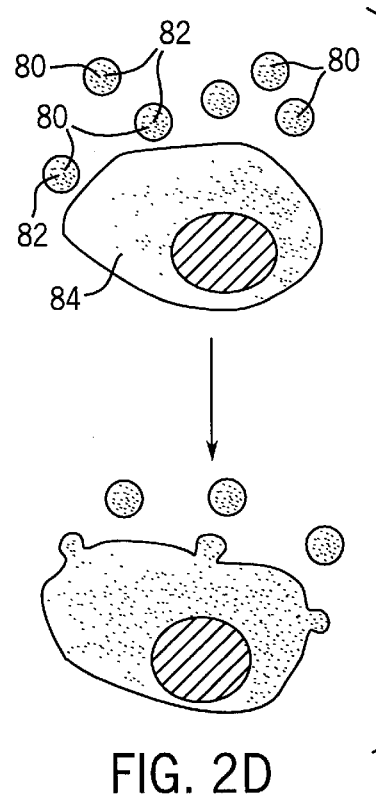

FIG. 2D depicts membrane bound vesicles 80 that are loaded with nanoprobes 82. The vesicles are induced to fuse with the target cell 84 at which point the nanoprobes migrate into the cell.

Figure 3:
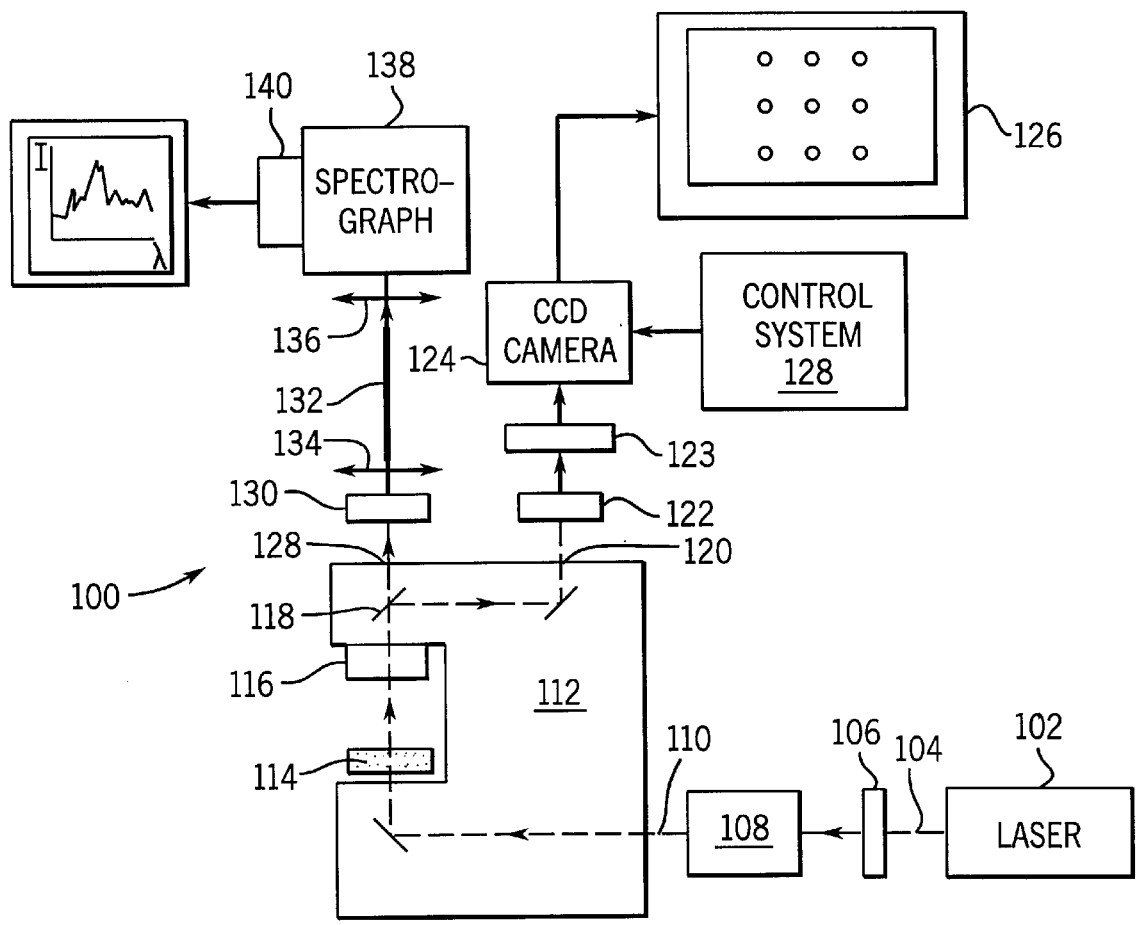
FIG. 3 is a block diagram of a spectral imaging surface-enhanced Raman scattering instrument.

After the nanoprobes have been introduced into the biological material to be studied, a Raman imaging system 100, such as the one in FIG. 3, is used to measure the SERS signals. The Raman imaging system 100 includes, for example, a 5 mW helium-neon laser 102 that produces an output beam 104 having a wavelength of 632.8 nm. The laser beam 104 passes through a bandpass filter 106 and then is expanded and recollimated using a spacial filter/beam expansion module 108. The resultant beam 110 enters a microscope system 112 where it is directed through the sample 114 containing the SERMED nanoprobes. In one embodiment, sample 114 may be a multiple microcell sample holder with each microcell containing a separate sample for high throughput drug screening or biomedical analysis. The light emitted by the sample 114 travels to an objective lens 116 that has an appropriate magnification. The objective lens focuses the light onto a beam splitter 118 which divides the light and sends a portion through a first exit port 120 of the microscope system 112.

The light from the first exit port passes through a holographic notch filter 122 which rejects the laser scatter and through an optical filter 123 that transmits the Raman signal. Filter 123 may be a bandpass filter or a tunable filter, such as an acousto-optic or liquid crystal tunable filter. The resultant beam is sent to a charge-coupled device (CCD) video camera 124 that produces a two-dimensional image which is presented to the operator on a video monitor 126. The CCD camera 124 is operated by a control system 128. The nanoprobe technology is very appropriate for high throughput analysis since nanoprobes can be used to analyze single cells. Therefore, very number of single cells can be analyzed in parallel. For example, the CCD camera with 1000×1000 pixels allows $10^6$ simultaneous analyses.

The other portion of the light from beam splitter 118 passes through a second exit port 128 of the microscope system 112 and is used to detect the SERS spectra from the sample 114. That portion of the light passes through a second holographic notch filter 130 to reject the laser scatter from the SERS emission and the resultant beam is focused through an optical fiber 132 by appropriate optics 134. Additional optics 136 at the output of the optical fiber 132 focuses the light onto the emission slit of a spectrograph 138, such as model HR320 manufactured by ISA. The spectrograph 138 is equipped with a thermo-electrically cooled, red-enhanced intensified CCD imager 140, such as model RE/ICCD 5765 manufactured by Princeton Instruments. If two-dimensional multi-spectral images are not required, a conventional Raman spectrometer may be used.

The use of SERMED nanoprobes extends the usefulness and application areas of SERS techniques considerably. Medical applications involve all the techniques that analyze intracellular environment inside single cells. In addition, SERMED nanoprobes can be ejected or implanted into a living organism to provide in situ self-contained nanoprobes to monitor the function of that organism.

Figure 4:
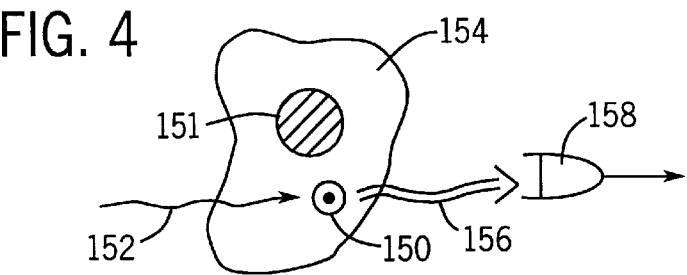
FIG. 4 illustrates a probe according to the present invention being irradiated by a light beam.

Appropriate chemical receptors or biological receptors can be designed so that the nanoprobes bind to specific targets inside cells. Electric or magnetic fields may be employed to move the nanoprobes (with magnetic cores) into desired environments inside cells. As shown in FIG. 4, the nanoprobe 150 adjacent cell nucleus 151 is irradiated by a light beam 152, such as from a laser outside the cell 154. Due to the short range of the SERS effect induced by the nanoprobes only cellular components absorbed on or near the nanoprobes experience the SERS effect, thereby producing the SERS signal 156 that is received by a detector 158.

An important advantage of the SERMED nanoprobe is the non-invasive method of excitation and detection. For example, near-infrared (NIR) excitation can penetrate tissue to excite the nanoprobe inside cells and tissue. The resulting SERS signal (red-shifted in wavelength) also is inside the NIR range so as to be emitted from the cells and tissue.

I claim:

1. A probe for a surface-enhanced Raman scattering spectroscopy, the probe comprising a body with a width less than one micrometer and a metallic coating which completely encapsulates the body and enhances Raman scattering during spectroscopic examination of a biological substance containing the probe.

2. The probe as recited in claim 1 wherein the body has a width in the range 10 to 500 nanometers.

3. The probe as recited in claim 1 wherein the body has a width in the range 10 to 100 nanometers.

4. The probe as recited in claim 1 wherein the body has substantially a spherical shape.

5. The probe as recited in claim 1 further comprises another coating selected from the group consisting of a bioreceptor and biomimetic material.

6. The probe as recited in claim 1 further comprises another coating selected from the group consisting of an antibody, an enzyme, a chemoreceptor, a microorganism, a tissue, an organelle and DNA.

7. The probe as recited in claim 1 wherein the body comprises a core of magnetic material surrounded by a metal coating.

8. The probe as recited in claim 1 wherein the body comprises a core of electrically charged material surrounded by a metal coating.

9. The probe as recited in claim 1 wherein the body comprises a first particle of metallic material abutting a second particle of non-metallic material.

10. The probe as recited in claim 9 wherein the first particle comprises material selected from the group consisting of a polymer, silica and titania.

11. The probe as recited in claim 9 further comprising a layer of material applied to one of the first particle and the second particle, wherein the material is selected from the group consisting of a polymer, a bioreceptor and biomimetic material.

12. The probe as recited in claim 9 further comprising a layer of material applied to one of the first particle and the second particle, wherein the material is selected from the group consisting of an antibody, an enzyme, a gene fragment, a chemoreceptor, a microorganism, a tissue, an organelle and DNA.

13. The probe as recited in claim 9 wherein the body comprises a core of non-metallic material and a plurality of metallic particles encrusted onto the core.

14. The probe as recited in claim 9 wherein the body comprises a core of non-metallic material enclosing a plurality of metallic particles.

15. The probe as recited in claim 13 further comprising a layer of material applied to one of the core and plurality of particles, wherein the material is selected from the group consisting of a polymer, a bioreceptor and biomimetic material.

16. The probe as recited in claim 1 further comprising another coating containing a gene fragment.

17. A method of surface-enhanced Raman spectroscopy comprising:

introducing a probe into a biological substance being examined, the probe comprising a body with a width less than one micrometer and having a metallic surface which enhances Raman scattering during spectroscopic examination;

exciting the biological substance with a source of radiation;

detecting the Raman emission emitted from the biological substance; and spectroscopically analyzing the Raman emission.

18. The method as recited in claim 17 wherein the source of radiation provides excitation in the near infrared spectrum.

19. The method recited in claim 17 wherein the source of radiation provides excitation at two different wavelengths.

20. The method as recited in claim 17 wherein introducing a probe into a biological substance comprises introducing the probe into a cell.

21. The method as recited in claim 17 further comprising producing a probe by coating a core of metallic material with material selected from the group consisting of biomimetic material, an antibody, an enzyme, a chemoreceptor, a microorganism, a tissue, an organelle and DNA.

22. The method as recited in claim 17 further comprising producing a probe by applying a metal coating to a core of material selected from the group consisting of magnetic material and electrically charged material.

23. The method as recited in claim 17 wherein detecting the Raman signal uses a two-dimensional detector.

24. The method as recited in claim 17 further comprising filtering a signal produced by detecting the Raman emission.

25. The method as recited in claim 17 wherein the filtering employs a tunable filter.

26. The method as recited in claim 17 wherein the filtering employs a tunable filter, selected from the group consisting of an acousto-optic tunable filter and a liquid crystal tunable filter.

27. The method as recited in claim 17 wherein the metallic surface of the probe is formed by a metallic coating which completely encapsulates the body.

28. The method as recited in claim 17 further comprising producing a probe by coating a core of metallic material with a polymer.

29. The method as recited in claim 17 further comprising producing a probe by coating a core of metallic material with a gene fragment.

* * * * *